United States Patent
Symons et al.

(10) Patent No.: US 6,562,747 B2
(45) Date of Patent: May 13, 2003

(54) GAS SENSOR ELECTROLYTE

(75) Inventors: Walter Thomas Symons, Grand Blanc, MI (US); Kaius Kiiren Polikarpus, Grand Blanc, MI (US); Kerry J. Gross, New Lothrop, MI (US); Da Yu Wang, Troy, MI (US); Paul Casey Kikuchi, Fenton, MI (US)

(73) Assignee: Delphi Technologies, Inc., Troy, MI (US)

( * ) Notice: Subject to any disclaimer, the term of this patent is extended or adjusted under 35 U.S.C. 154(b) by 32 days.

(21) Appl. No.: 09/741,498

(22) Filed: Dec. 19, 2000

(65) Prior Publication Data
US 2002/0108872 A1 Aug. 15, 2002

(51) Int. Cl.⁷ .................. H01M 8/10; C04B 35/48
(52) U.S. Cl. ................. 501/103; 501/105; 429/33
(58) Field of Search ................. 501/103, 105, 501/134; 252/62.2; 429/33

(56) References Cited

U.S. PATENT DOCUMENTS

| | | | | |
|---|---|---|---|---|
| 4,266,979 A | * | 5/1981 | Miyoshi et al. | |
| 4,542,110 A | * | 9/1985 | Nakada et al. | 501/103 |
| 5,045,511 A | * | 9/1991 | Bosomworth et al. | |
| 5,087,595 A | * | 2/1992 | Marsh et al. | 501/105 |
| 5,242,873 A | * | 9/1993 | Singh et al. | 501/103 |
| 5,795,545 A | | 8/1998 | Koripella et al. | 422/94 |
| 6,121,177 A | * | 9/2000 | Guigonis et al. | |

OTHER PUBLICATIONS

U.S. patent application Ser. No. 09/767,925, Polikarpus et al., filed Dec. 19, 2000.
http://www.zrchem.com/zelem.htm, Oct. 2, 2000.
http://www.tosoh.com/EnglishHomePage/tcdiv/tcdad-cer.htm, Nov. 17, 2000.

* cited by examiner

Primary Examiner—Christopher A. Fiorilla
(74) Attorney, Agent, or Firm—Vincent A. Cichosz

(57) ABSTRACT

The electrolyte comprises up to about 80 wt % zirconia, up to about 30 wt % stabilizer, and up to about 40 wt % dopant-zirconia. Alternatively, the electrolyte can comprise zirconia having a phase chemistry, wherein the phase chemistry, at about 25° C., is about 15 wt % to about 35 wt % monoclinic, less than about 10 wt % tetragonal, balance cubic, based upon the weight of the zirconia in the electrolyte.

10 Claims, 3 Drawing Sheets

GAS SENSOR ELECTROLYTE

TECHNICAL FIELD

The present disclosure relates to gas sensors, and particularly to the electrolyte of a sensor.

BACKGROUND

The automotive industry has used exhaust gas sensors in vehicles for many years to sense the composition of exhaust gases, namely, oxygen. For example, a sensor is used to determine the exhaust gas content for alteration and optimization of the air to fuel ratio for combustion.

One type of sensor uses an ionically conductive solid electrolyte between porous electrodes. For oxygen, solid electrolyte sensors are used to measure oxygen activity differences between an unknown gas sample and a known gas sample. In the use of a sensor for automotive exhaust, the unknown gas is exhaust and the known gas, (i.e., reference gas), is usually atmospheric air because the oxygen content in air is relatively constant and readily accessible. This type of sensor is based on an electrochemical galvanic cell operating in a potentiometric mode to detect the relative amounts of oxygen present in an automobile engine's exhaust. When opposite surfaces of this galvanic cell are exposed to different oxygen partial pressures, an electromotive force ("emf") is developed between the electrodes according to the Nernst equation.

With the Nernst principle, chemical energy is converted into electromotive force. A gas sensor based upon this principle typically consists of an ionically conductive solid electrolyte material, a porous electrode with a porous protective overcoat exposed to exhaust gases ("exhaust gas electrode"), and a porous electrode exposed to a known gas' partial pressure ("reference electrode"). Sensors typically used in automotive applications use a yttria stabilized zirconia based electrochemical galvanic cell with porous platinum electrodes, operating in potentiometric mode, to detect the relative amounts of a particular gas, such as oxygen for example, that is present in an automobile engine's exhaust. Also, a typical sensor has a ceramic heater attached to help maintain the sensor's ionic conductivity. When opposite surfaces of the galvanic cell are exposed to different oxygen partial pressures, an electromotive force is developed between the electrodes on the opposite surfaces of the zirconia wall, according to the Nernst equation:

$$E = \left(\frac{-RT}{4F}\right) \ln\left(\frac{P_{O_2}^{ref}}{P_{O_2}}\right)$$

where
E=electromotive force
R=universal gas constant
F=Faraday constant
T=absolute temperature of the gas
$P_{O_2}^{ref}$=oxygen partial pressure of the reference gas
$P_{O_2}$=oxygen partial pressure of the exhaust gas Due to the large difference in oxygen partial pressure between fuel rich and fuel lean exhaust conditions, the electromotive force (emf) changes sharply at the stoichiometric point, giving rise to the characteristic switching behavior of these sensors. Consequently, these potentiometric oxygen sensors indicate qualitatively whether the engine is operating fuel-rich or fuel-lean, conditions without quantifying the actual air-to-fuel ratio of the exhaust mixture.

For example, an oxygen sensor, with a solid oxide electrolyte such as zirconia, measures the oxygen activity difference between an unknown gas and a known reference gas. Usually, the known reference gas is the atmosphere air while the unknown gas contains the oxygen with its equilibrium level to be determined. Typically, the sensor has a built in reference gas channel which connects the reference electrode to the ambient air. To avoid contamination of the reference air by the unknown gas, the sensor requires expensive sensor package that usually has complex features in order to provide sufficient gas sealing between the reference air and the unknown gas. Alternatively, in-situ electrochemical oxygen pumping can be used. In this method, the air reference electrode chamber is replaced by a sealed reference electrode with oxygen electrochemically pumped in from the exhaust gas. This method eliminates the exhaust gas contamination problem but creates its own drawbacks. That is, an expensive electronic circuit is required to do the electrochemical oxygen pumping.

Manufacturing techniques used to create gas sensors continue to evolve with the goal of providing a more durable sensor that will be resistant to cracking as a result of temperature cycling, while decreasing the cost. Accordingly, there remains a need in the art for a low cost, temperature resistant sensor.

SUMMARY

The drawbacks and disadvantages of the prior art are overcome by the gas sensor electrolyte and method for making the same. The electrolyte comprises up to about 80 wt % monoclinic zirconia, up to about 30 wt % stabilizer, and up to about 40 wt % dopant-zirconia.

The method of making an electrolyte, comprises blending monoclinic zirconia powder with a co-precipitated stabilized zirconia and stabilizer to form a mixture; and forming an electrolyte from the mixture.

BRIEF DESCRIPTION OF THE DRAWINGS

The gas sensor will now be described, by way of example only, with reference to the accompanying drawings, which are meant to be exemplary, and not limiting.

DESCRIPTION OF THE PREFERRED EMBODIMENT

Although described in connection with an oxygen sensor, it is to be understood that the sensor could be a nitrogen oxide sensor, hydrogen sensor, hydrocarbon sensor, or the like. Furthermore, while oxygen is the reference gas used in the description disclosed herein, it should be understood that other gases could be employed as a reference gas.

The sensor comprises an electrolyte; a sensing electrode capable of sensing an exhaust gas, with a first side disposed on and in intimate contact with a first side of the electrolyte; a reference electrode capable of sensing a reference gas, with a first side disposed on and in intimate contact with the second side of the electrolyte; a protective layer with a first side disposed adjacent to the second side of the sensing electrode, and optionally a protective coating disposed on the second side of the protective layer.

Figure 1:
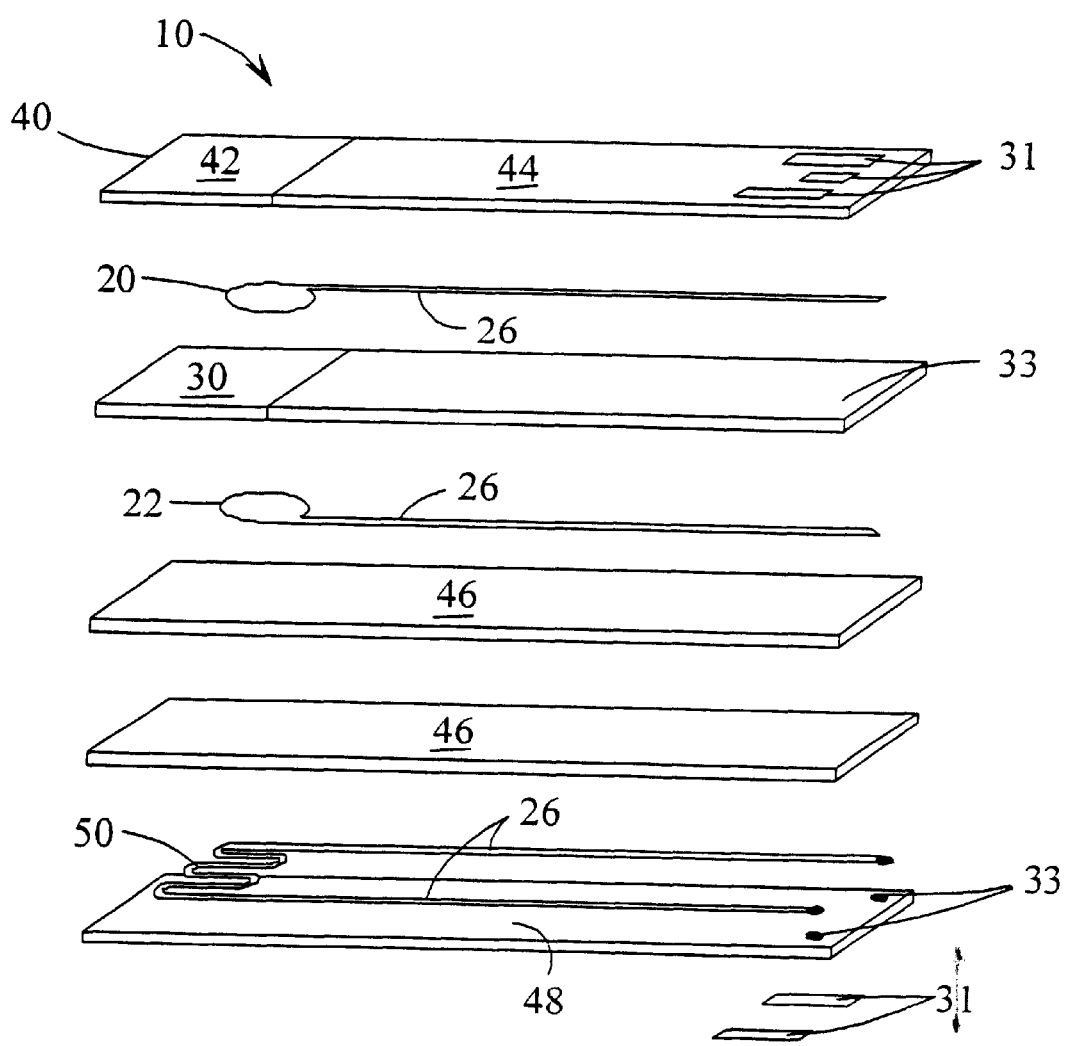
FIG. 1 is a layout of a planar gas sensor.

Referring to FIG. 1, the sensor element 10 is illustrated. Although a planar sensor design is illustrated, the sensor can be conical, or any known design. The sensing or exhaust gas electrode 20 and the reference or reference gas electrode 22 are disposed on opposite sides of, and adjacent to, an electrolyte layer 30 creating an electrochemical cell (20/30/22). On the side of the sensing electrode 20 opposite electrolyte 30 is a protective insulating layer 40 having a dense section 44 and a porous section 42 that enables fluid communication between the sensing electrode 20 and the exhaust gas. Meanwhile, disposed on a second side of the reference electrode 22 is heater 50 for maintaining sensor element 10 at the desired operating temperature. Typically disposed in contact with the heater 50 are one or more insulating layers 46, with an additional protective layer 48 disposed on a side of heater 50 opposite insulating layer 46.

In addition to the above sensor components, conventional components can be employed, including but not limited to protective coatings (e.g., spinel, alumina, magnesium aluminate, and the like, as well as combinations comprising at least one of the foregoing coatings), lead gettering layer (s), leads 26, contact pads 31, ground plane(s), support layer(s), additional electrochemical cell(s), and the like. The leads 26, which supply current to the heater and electrodes, are typically formed on the same layer as the heater/electrode to which they are in electrical communication and extend from the heater/electrode to the terminal end of the gas sensor where they are in electrical communication with the corresponding via 33 and appropriate contact pads 31.

Insulating layers 46, and protective layers 48, 40 provide structural integrity (e.g., protect various portions of the gas sensor from abrasion, vibration, and the like, and provide physical strength to the sensor), and physically separate and electrically isolate various components. These layer(s), which can be formed using ceramic tape casting methods or other methods such as plasma spray deposition techniques, screen printing, stenciling and others conventionally used in the art, can each be up to about 200 microns thick or so, with a thickness of about 50 microns to about 200 microns preferred. Since the materials employed in the manufacture of gas sensors preferably comprise substantially similar coefficients of thermal expansion, shrinkage characteristics, and chemical compatibility in order to minimize, if not eliminate, delamination and other processing problems, the particular material, alloy or mixture chosen for the insulating and protective layers is dependent upon the specific electrolyte employed. Typically these insulating layers comprise a dielectric material such as alumina, and the like.

Disposed between insulating layers, 46, and protective layer 48, is a heater 50 that is employed to maintain the sensor element at the desired operating temperature. Heater 50 can be any conventional heater capable of maintaining the sensor end at a sufficient temperature to facilitate the various electrochemical reactions therein. The heater 50, which is typically platinum, palladium, and the like, as well as mixtures and alloys comprising at least one of the foregoing metals, or any other conventional heater, is generally screen printed or otherwise disposed onto a substrate to a thickness of about 5 microns to about 50 microns.

Disposed on an opposite side of insulating layers 46 is electrolyte layer 30. Electrolyte layer 30 is solid, can comprise the entire layer or a portion thereof, can be any material that is capable of permitting the electrochemical transfer of oxygen ions, should have an ionic/total conductivity ratio of approximately unity, and should be compatible with the environment in which the gas sensor will be utilized (e.g., up to about 1,000° C.). Although the electrolyte material disclosed herein is zirconia, any electrolyte possessing thermal expansion characteristics similar in nature (i.e. hysteresis) can be employed. It should be noted that the electrolyte layer 30 and porous section 42 can comprise an entire layer or a portion thereof; e.g., they can form the layer, be attached to the layer (porous section/electrolyte abutting dielectric material), or disposed in an opening in the layer (porous section/electrolyte can be an insert in an opening in a dielectric material layer). The latter arrangement eliminates the use of excess electrolyte and protective material, and reduces the size of gas sensor by eliminating layers. Any shape can be used for the electrolyte and porous section, with the size and geometry of the various inserts, and therefore the corresponding openings, being dependent upon the desired size and geometry of the adjacent electrodes. It is preferred that the openings, inserts, and electrodes have a substantially compatible geometry such that sufficient exhaust gas access to the electrode(s) is enabled and sufficient ionic transfer through the electrolyte is established.

In order to control the coefficient of thermal expansion ("CTE") of the electrolyte, a stabilizer can be employed. CTE control is attained, in a zirconia electrolyte, by controlling the phase transformation of the zirconia during thermal cycling. Uncontrolled phase transformation of the tetragonal phase to a monoclinic phase upon cooling of the electrolyte is undesirable because such a transformation causes excessive volume expansion. Too much volume expansion and/or contraction does not allow the co-fired alumina support layers to remain adhered to the electrolyte, and will cause cracking of the zirconia electrolyte. By carefully controlling the phase transformations in the zirconia, the desired thermal expansion can be obtained.

CTE control can be achieved by controlling stabilizer distribution within the zirconia prior to firing. For example, by seeding the typical electrolyte material with a zirconia powder that has been co-precipitated with a dopant, the desired phase chemistry can be obtained at a lower firing temperature. Preferably, the phase chemistry is sufficiently controlled to attain an electrolyte comprising a phase chemistry of about 15 weight percent (wt %) to about 35 wt % monoclinic, less than about 10 wt % tetragonal phase, balance cubic phase, based upon the weight percent of zirconia in the electrolyte at room temperature (e.g., about 25° C.). More preferably, the phase chemistry, under the same conditions comprises about 20 to about 30 wt % monoclinic, less than about 8 wt % tetragonal, balance cubic more preferred, and about 20 wt % to about 26 wt % monoclinic, less than about 5 wt % tetragonal, balance cubic. This phase composition can be attained with an electrolyte comprising up to about 80 wt % monoclinic zirconia, up to about 30 wt % stabilizer, and up to about 40 wt % co-precipitated, dopant stabilized zirconia ("dopant-zirconia"), with about 40 to about 70 wt % monoclinic zirconia, about 5 to about 25 wt % stabilizer, and about 20 to about 40 wt % dopant-zirconia preferred, and about 50 to 70 wt % monoclinic zirconia, about 5 to about 15 wt % stabilizer, and about 25 to about 35 wt % dopant-zirconia more preferred, based upon the total weight of the electrolyte.

The electrolyte, e.g., zirconia, can be stabilized with a stabilizer such as calcium, barium, yttrium, magnesium, aluminum, lanthanum, cesium, gadolinium, and the like, as well as oxides and combinations comprising at least one of the foregoing materials. Preferably, the stabilizer comprises up to about 15 wt % yttria and up to about 15 wt % alumina, based on the total weight of the electrolyte, with about 3 to about 15 wt % yttria and about 2 to about 10 wt % alumina more preferred, and about 3 wt % to about 10 wt % yttria and about 2 wt % to about 5 wt % alumina most preferred.

The dopant-zirconia which is combined with the zirconia and stabilizer, preferably comprises a dopant which has been co-precipitated with the zirconia. Typically, the zirconia can be co-precipitated with up to about 15 mole percent (mol %) dopant, based on 100 mol % dopant-zirconia, with about 4 to about 12 mol % dopant preferred and about 5 to about 10 mol % dopant especially preferred. Possible dopant materials include, but are not limited to, calcium, barium, yttrium, magnesium, aluminum, lanthanum, cesium, gadolinium, and the like, as well as oxides and combinations comprising at least one of the foregoing dopants.

The average particle size and particle surface area of the dopant-zirconia powder can be controlled by subsequently calcining the powder. For example, by calcining a zirconia powder that had been co-precipitated with about 8 mol % yttria at a temperature of about 1150° C. to about 1200° C. for about 1 hour, the average particle size can be increased from about 0.3 microns to about 0.8 microns and the average particle surface area can be decreased from about 14 $m^2/g$ to about 3.9 $m^2/g$. This secondary process decreases the reactivity of the co-precipitated zirconia, thus enabling the powder to sinter at a slower rate. The temperature and time of this secondary calcining process can be altered to achieve the desired sintering properties of the dopant-zirconia powder.

Typically, the electrolyte, which can be formed via many conventional processes (e.g., die pressing, roll compaction, stenciling and screen printing, tape casting techniques, and the like), where the monoclinic zirconia, stabilizer(s), and dopant-zirconia powders are combined in a solvent, disposed into a layer and dried. The layer typically has a thickness of up to about 500 microns or so, with a thickness of about 25 microns to about 500 microns preferred, and a thickness of about 50 microns to about 200 microns especially preferred. The resulting electrolyte can be fired or co-fired at a temperature up to about 1,550° C., preferably at a temperature of about 1,400° C. to about 1,500° C., and more preferably at a temperature of about 1,400° C. to about 1,450° C. Specific firing temperature can be manipulated to arrive at the desired CTE in the final zirconia body by adjusting the total content of "dopant zirconia"

The electrodes 20, 22, are disposed in ionic contact with the electrolyte layer 30. Conventional electrodes can comprise any catalyst capable of ionizing oxygen, including, but not limited to, metals such as platinum, palladium, osmium, rhodium, iridium, gold, ruthenium, zirconium, yttrium, cerium, calcium, aluminum, and the like, other materials, such as silicon, and the like; and mixtures, oxides, alloys, and cermets comprising at least one of the foregoing catalysts. As with the electrolyte, the electrodes 20, 22 can be formed using conventional techniques. Some possible techniques include sputtering, painting, chemical vapor deposition, electroless deposition, screen printing, and stenciling, among others. If a co-firing process is employed for the formation of the sensor, screen printing the electrodes onto appropriate tapes is preferred due to simplicity, economy, and compatibility with the co-fired process. Electrode leads 26, 27 and vias 33 in the insulating and/or electrolyte layers are typically formed simultaneously with electrodes.

Once the sensor has been formed, it can be disposed in an exhaust stream, wherein one of the electrodes is in contact with an exhaust gas and one of the electrodes is in contact with a reference gas, such as oxygen. The relative amount of oxygen in the exhaust gas can then be detected.

The following examples are provided to further illustrate the electrolyte and is not intended to limit the scope thereof.

EXAMPLES

Example 1

A mixture comprising about 87.6 wt % monoclinic zirconia, about 8.6 wt % yttria and about 3.8 wt % alumina was prepared. The zirconia comprised an average particle size of about 0.7 microns, and specific surface area of about 2 $m^2/g$. The yttria comprised an average particle size of about 2 microns. The mixture was tape casted to form a green body 1 inch wide and ¼ inch thick and fired at a temperature of about 1,510° C.

Examples 2–6

All Use the Same Monoclinic Zirconia, Yttria, and Alumina Powders

Example 2

A mixture comprising about 87.6 wt % monoclinic zirconia, about 8.6 wt % yttria and about 3.8 wt % alumina was prepared. The zirconia comprised an average particle size of about 0.3 microns, and specific surface area of about 14 $m^2/g$. The yttria comprised an average particle size of about 1 micron. The alumina was of a higher purity as compared to the alumina used in Example 1. The mixture was tape casted to form a green body 1 inch wide and ¼ inch thick and fired at a temperature of about 1,510° C.

Example 3

A mixture of Example 2 was tape casted to form a green body 1 inch wide and ¼ inch thick and fired at a temperature of about 1,450° C.

Example 4

A mixture of Example 2 was tape casted to form a green body 1 inch wide and ¼ inch thick and fired at a temperature of about 1,410° C.

Example 5

A mixture comprising about 65.7 wt % monoclinic zirconia, about 6.4 wt % yttria, about 2.9 wt % alumina, and about 25 wt % co-precipitated zirconia (8 mol % yttria co-precipitated with zirconia; average particle size of about 0.3 microns) was prepared. The monoclinic zirconia comprised an average particle size of about 0.3 microns, and specific surface area of about 14 $m^2/g$. The yttria comprised an average particle size of about 1 microns. The co-precipitated zirconia comprised an average particle size of about 0.3 microns and an average particle surface area of about 13 $m^2/g$. The mixture was tape casted to form a green body 1 inch wide and ¼ inch thick and fired at a temperature of about 1,450° C.

Example 6

The samples prepared in accordance with Examples 1–6 were measured for the amount of monoclinic zirconia present by X-ray diffraction. Table I lists the results of the X-ray diffraction test:

TABLE I

Summary of X-ray Diffraction Tests

| Sample Prepared By: | Zirconia Monoclinic Phase (wt %) |
|---|---|
| Example 1 | 20 |
| Example 2 | 29.9 |
| Example 3 | 35 |
| Example 4 | 38.6 |
| Example 5 | 25.5 |
| Example 6 | 25.7 |

The results of the X-ray diffraction tests indicate that the sample prepared in accordance with Examples 5, and 6 possess lower amounts of monoclinic zirconia. The reduction in monoclinic content is achieved at lower firing temperatures. When the body of Examples 2, 3 and 4 are fired at 1,510° C., 1,450° C. and 1,410° C. respectively the monoclinic content of the body increases with lower firing temperature. The monoclinic content of Example 2 is already greater in value than that of Example 1 even though both possess the same base formulation. The compositions of Examples 5 and 6 are closer in monoclinic content to that of Example 1 while being fired at significantly lower temperatures.

Figure 2:
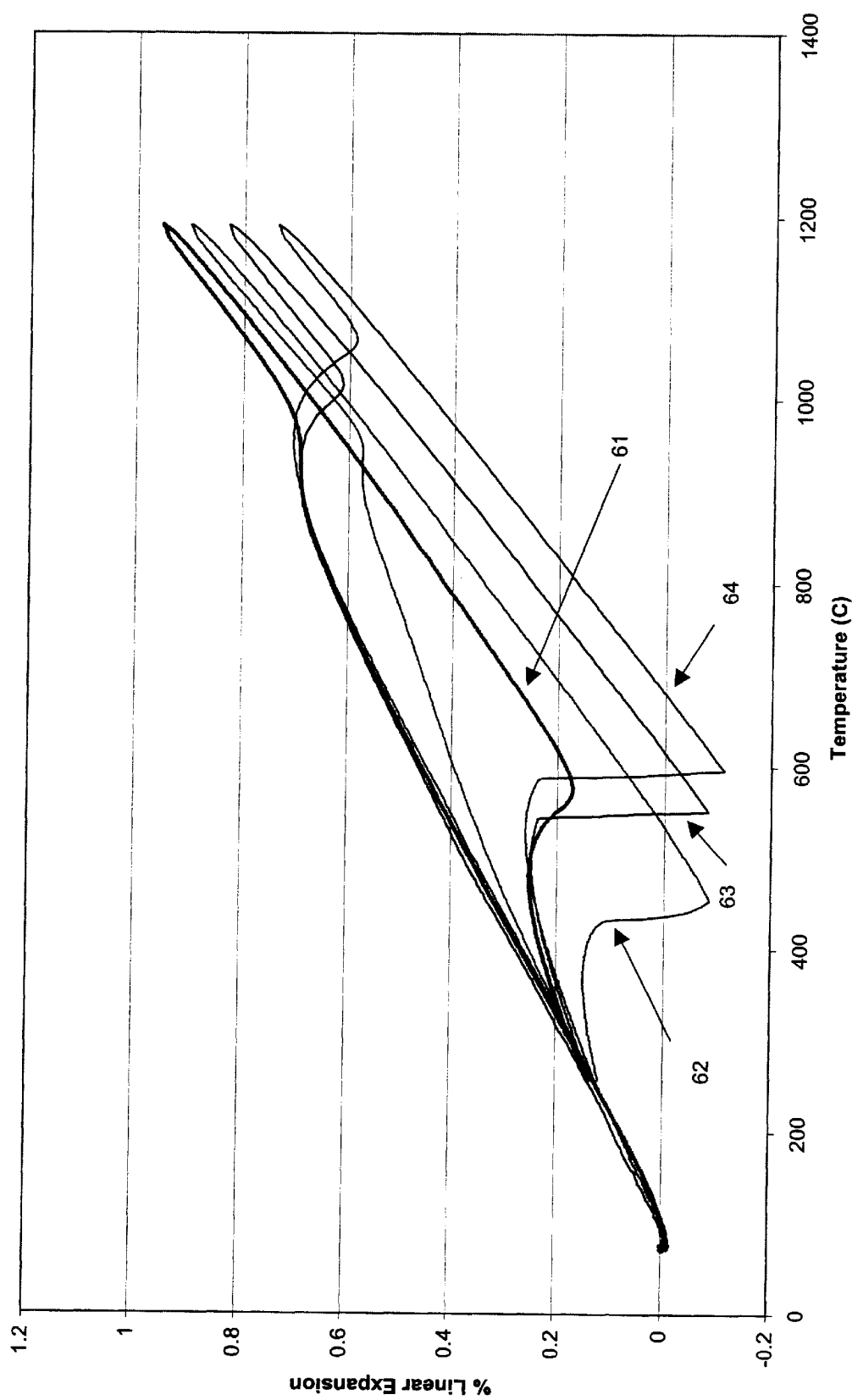
FIG. 2 illustrates the linear expansion of an electrolyte of a planar gas sensor as a function of temperature.
Figure 3:
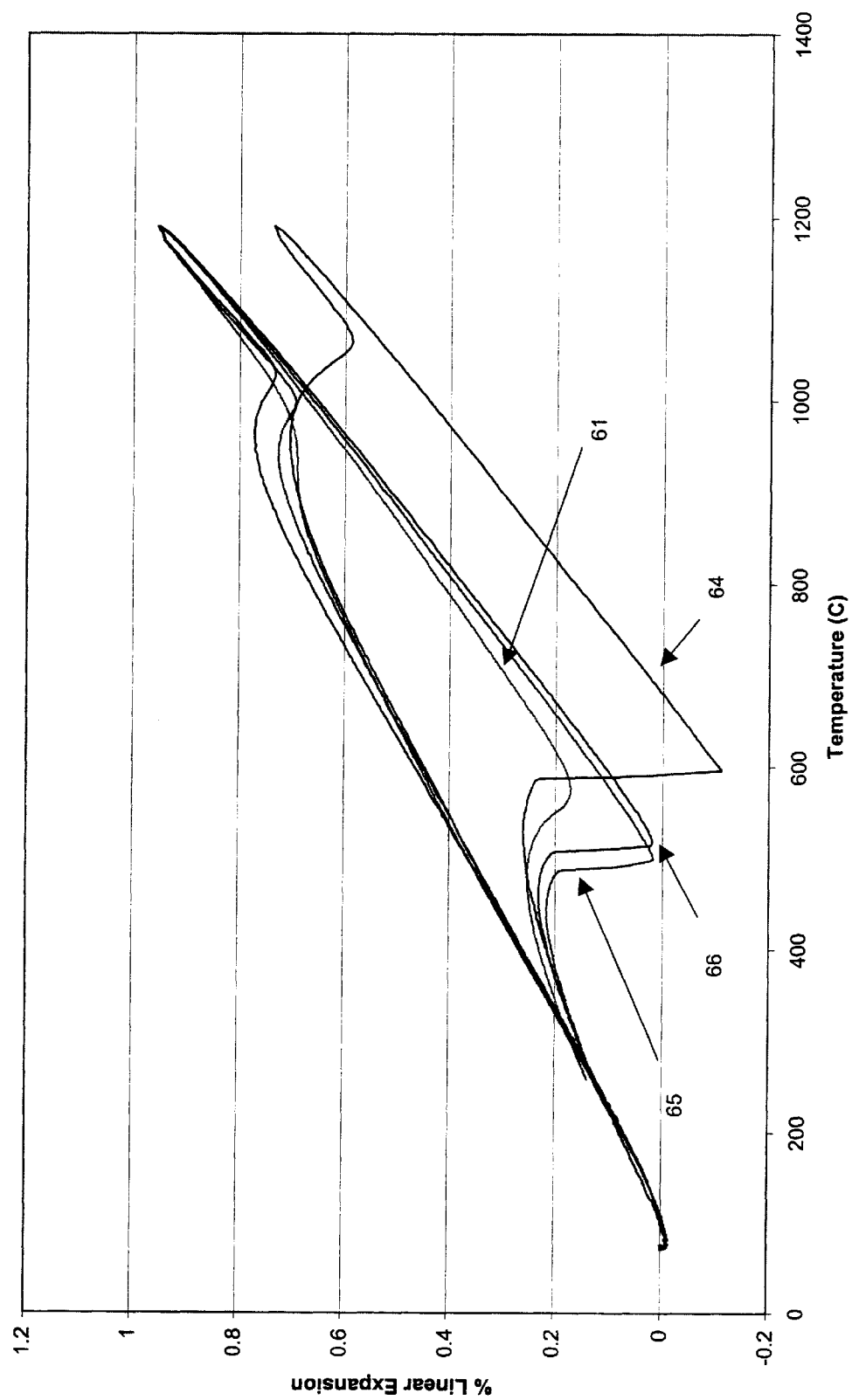
FIG. 3 illustrates the linear expansion of an electrolyte of a planar gas sensor as a function of temperature.

The samples prepared in accordance with Examples 1–6 were each placed in a dilatometer. The linear expansion of the sample was measured while the temperature was increased to 1,200° C., then decreased to room temperature. The results of these tests are illustrated in FIG. 2 for bodies prepared according to Examples 1, 2, and 3. It is desirable to have an electrolyte that possesses the hysteresis characteristics of Example 1. These characteristics permit the co-firing of the alumina and zirconia layers comprising the sensor, as well as permitting the sensor to have acceptable thermal durability. Significant variation from this hysteresis characteristic does not allow sufficient compatibility between the zirconia and alumina to permit co-firing. The hysteresis properties of the electrolyte prepared in accordance with Example 5 represented by line 65 and that of Example 6 represented by line 66, as shown in FIG. 3, are similar to the hysteresis properties of the electrolyte prepared in accordance with Example 1, represented by line 61, which is shown in both FIGS. 2 and 3. The hysteresis curves of Examples 2, 3, and 4 are represented by lines 62, 63 and 64 respectively, which are shown either in FIG. 2 and/or in FIG. 3. It is important to note that the firing temperature used in Example 5 was about 60° less than the firing temperature used in Example 1. Also, the firing temperature of Example 6 was about 100° less than the firing temperature used in Example 1.

Electrolytes prepared from the aforementioned compositions and method will be more likely to stay adhered to alumina layers when co-fired and will therefore be less likely to crack and cause the sensor to fail. Also, the firing temperature for the electrolyte can be drastically reduced, thus reducing the manufacturing costs of the sensors.

While preferred embodiments have been shown and described, various modifications and substitutions may be made thereto without departing from the spirit and scope of the invention. Accordingly, it is to be understood that the present invention has been described by way of illustration only, and such illustrations and embodiments as have been disclosed herein are not to be construed as limiting to the claims.

What is claims is:

1. An electrolyte, comprising:
   about 40 wt % to about 70 wt % monoclinic zirconia;
   about 40 wt % to about 25 wt % stabilizer; and
   about 20 wt % to about 40 wt % co-precipitated, dopant-zirconia.

2. The electrolyte of claim 1, comprising about 50 wt % to about 70 wt % monoclinic zirconia, about 5 wt % to about 15 wt % stabilizer, and about 25 wt % to about 35 wt % dopant-zirconia.

3. The electrolyte of claim 1, wherein the stabilizer comprises up to about 15 wt % yttria and up to about 15 wt % alumina, based on the total weight of the electrolyte.

4. The electrolyte of claim 3, wherein the stabilizer comprises about 3 wt % to about 15 wt % yttria and about 2 wt % to about 10 wt % alumina, based on the total weight of the electrolyte.

5. The electrolyte of claim 4, wherein the stabilizer comprises about 3 wt % to about 10 wt % yttria and about 2 wt % to about 5 wt % alumina, based on the total weight of the electrolyte.

6. The electrolyte of claim 1, wherein the dopant-zirconia comprises up to about 15 mol % dopant, based on 100 mol % dopant-zirconia.

7. The electrolyte of claim 6, wherein the dopant-zirconia comprises about 4 mol % to about 12 mol % dopant, based on 100 mol % dopant-zirconia.

8. The electrolyte of claim 7, wherein the dopant-zirconia comprises about 5 mol % to about 10 mol % dopant, based on 100 mol % dopant-zirconia.

9. The electrolyte of claim 6, wherein the dopant comprises a material selected from the group of calcium, barium, yttrium, magnesium, aluminum, lanthanum, cesium, gadolinium, and oxides and combinations comprising at least one of the foregoing materials.

10. The electrolyte of claim 9, wherein the dopant comprises yttria.

* * * * *